United States Patent [19]

Ward et al.

[11] 4,406,903

[45] Sep. 27, 1983

[54] XANTHINE DERIVATIVES USEFUL AS ANTIDEPRESSIVES

[75] Inventors: Terence J. Ward, Slough; Martyn D. Wood, Reading; Michael G. Wyllie, Maidenhead, all of England

[73] Assignee: John Wyeth and Brother Limited, Maidenhead, England

[21] Appl. No.: 338,929

[22] Filed: Jan. 12, 1982

[30] Foreign Application Priority Data

Jan. 21, 1981 [GB] United Kingdom ............... 8101820

[51] Int. Cl.$^3$ ............... A61K 31/52; C07D 473/06; C07D 473/08
[52] U.S. Cl. .................. 424/253; 544/268
[58] Field of Search .................. 544/268; 424/253

[56] References Cited

U.S. PATENT DOCUMENTS 3,247,203  4/1966  Barré et al. ............... 544/268
3,350,400  10/1967  Suter et al. ............... 424/253
3,637,696  1/1972  Otto ............... 424/253 X
4,144,340  3/1979  Offermanns et al. ............... 424/253

FOREIGN PATENT DOCUMENTS 347193  8/1960  Switzerland ............... 544/277

OTHER PUBLICATIONS

Shaw, Lancet, May 23, 1970, p. 1111.
Physicians' Desk Reference, 34 ed., Medical Economics Co., Oradell, N.J., p. 1241, 1980.

*Primary Examiner*—Donald G. Daus
*Assistant Examiner*—Diana G. Rivers
*Attorney, Agent, or Firm*—Richard K. Jackson

[57] ABSTRACT

Xanthine derivatives are provided which exhibit psychotropic activity in that they inhibit 5-hydroxytryptamine reuptake in vitro and are indicated for antidepressive use.

8 Claims, No Drawings

XANTHINE DERIVATIVES USEFUL AS ANTIDEPRESSIVES

The invention relates to xanthine derivatives, a process for their preparation and pharmaceutical compositions containing them.

The invention provides new compounds having the general formula I

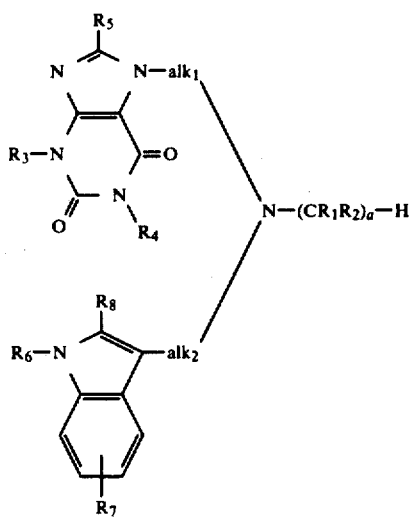

and their pharmaceutically acceptable salts, wherein $alk_1$ and $alk_2$ are, independently, lower alkylene which may be a straight or branched chain;

either one or both of $alk_1$ and $alk_2$ includes a hydrogen atom carried by the carbon atom linked directly to the nitrogen atom bearing $—(CR_1R_2)_a—H$;

$R_1$ and $R_2$ are, independently, hydrogen or alkyl;

$R_1$ and $R_2$ being such that $—CHR_1R_2$ is lower alkyl; a is 0 or 1 (i.e. $—(CH_1R_2)_a—H$ is hydrogen or lower alkyl);

$R_3$, $R_4$, $R_5$, $R_6$ and $R_8$ are, independently, hydrogen or lower alkyl; and $R_7$ is hydrogen, hydroxy, lower alkoxy, aryl(lower)alkoxy, lower alkyl, halogen, trifluoromethyl or di(-lower alkyl)amino.

By the term "lower" as used herein to refer to such groups as alkyl, alkylene and alkoxy, there is meant that the group contains 1 to 6 carbon atoms preferably 1 to 4 carbon atoms.

The lower alkylene groups represented by $alk_1$ and $alk_2$ may have straight or branched chains. Examples include methylene, methylmethylene, ethylmethylene, dimethylmethylene (in the case of one of $alk_1$ and $alk_2$) ethylene, propylene, trimethylene and tetramethylene. Ethylene and trimethylene are preferred.

$R_1$ and $R_2$ are hydrogen or alkyl such that $—CHR_1R_2$ is lower alkyl, for instance, methyl, ethyl, propyl, isopropyl, butyl etc. $R_1$ and $R_2$ are preferably hydrogen or methyl. The symbol a, which may represent 0 or 1, preferably represents 0.

The symbols $R_3$, $R_4$, $R_5$, $R_6$ and $R_8$ are, independently, hydrogen or lower alkyl, for instance, methyl, ethyl, propyl, isopropyl, butyl etc. As lower alkyl, methyl is preferred.

$R_7$ represents hydrogen, hydroxy, lower alkoxy, (for instance, methoxy, ethoxy, propoxy, isopropoxy, butoxy etc), aryl(lower)alkoxy (preferably phenyl(lower-)alkoxy, for instance benzyloxy or phenethyloxy), lower alkyl (for instance methyl, ethyl, propyl, isopropyl, butyl etc.), halogen (for instance chlorine or bromine), trifluoromethyl or di(lower alkyl)amino (for instance dimethylamino, ethylmethylamino or diethylamino). $R_7$ is preferably hydroxy, lower alkoxy or aryl(-lower)alkoxy in the 5-position of the indole system.

The salts of the invention are primarily acid addition salts. Examples of acid addition salts are these formed from inorganic and organic acids and include the sulphate, sulphonates (for instance the methanesulphonate and p-toluenesulphonate), acetate, maleate, fumarate, tartrate, malonate, citrate, formate and halides. The salts of the invention may also be, for instance, alkali metal salts derived from the compound having formula I where $R_7$ is hydroxy.

Examples of compounds accordng to the invention include 5-hydroxy-N-[3-(theophyllin-7-yl)propyl]tryptamine, 5-hydroxy-N-[3-(xanthin-7-yl)propyl]tryptamine, 5-hydroxy-N-[2-(theophyllin-7-yl)ethyl]tryptamine, their methyl, ethyl and benzyl ethers, N-[3-(theophyllin-yl-7-yl)propyl]tryptamine and the pharmaceutically acceptable salts thereof.

The compounds having formula I and their pharmaceutically acceptable salts are pharmaceutically useful. In particular they exhibit psychotropic activity in that they inhibit 5-hydroxytryptamine reuptake in vitro and are indicated for antidepressive use.

Compounds may be evaluated for activity according to the following procedure:

PROCEDURE 1

Inhibition of 5-Hydroxytryptamine or Noradrenaline Uptake in Brain Slices

Two rates (weighing 170–200 g) are decapitated and the brains rapidly removed and placed in ice-cold Krebs solution. The cerebral cortex on each side of the median line is opened out flat and cut to give two slabs of even thickness. The slabs are weighed and then sliced on a McIlwain tissue chopper. The tissue is sliced twice, the second cutting being at an angle of 45° to the first. The interval of cutting is 0.1 mm. The slices are transferred to a 5 ml conical flask and Krebs solution is added in the proportion 5 ml/g tissue. The slices are dispersed in the solution by sucking up and down in a Pasteur pipette. When a satisfactory suspension is achieved it is pipetted in 50 μl portions into 25 ml conical flasks containing 4.5 ml chilled Krebs solution. An Eppendorf pipette with the tip cut back to about 1 mm diameter is used. The suspension is kept well mixed at this stage so that each portion taken contains the same amount of tissue (~10 mg). The flasks are gassed with 95% $O_2$/5% $CO_2$ and sealed with aluminium foil. They are then placed in a water bath at 27° for 15 minutes pre-incubation.

Flasks in groups of four are then each treated by an addition in 0.5 ml. to achieve the following concentrations in the medium.

| GROUP | $^3H$ 5-HYDROXY-TRYPTAMINE CONCENTRATION | COMPOUND (CONCENTRATION) |
|---|---|---|
| A | $10^{-7}$ M | TEST COMPOUND ($10^{-5}$ M) |
| B | $10^{-7}$ M | IMIPRAMINE ($10^{-5}$ M) |
| C | $10^{-7}$ M | IMIPRAMINE ($10^{-6}$ M) |
| D | $10^{-7}$ M | IMIPRAMINE ($10^{-7}$ M) |
| E | $10^{-7}$ M | — |
| F | NO ADDITION AT | |

| GROUP | $^3$H 5-HYDROXY-TRYPTAMINE CONCENTRATION | COMPOUND (CONCENTRATION) |
|---|---|---|
| | THIS STAGE | |

After 20 minutes incubation the slices are filtered off in filter funnels connected to a vacuum line. Each flask in rinsed with 5 ml Krebs which is also poured through the filter funnel followed by a further 5 ml Krebs. For group F the treatment differs in that $^3$H 5-hydroxytryptamine in 0.5 ml is added immediately before filtration. This gives an estimation of the amount of activity retained by the filter from the solution together with the amount of non-specific binding by the tissue.

The filter papers are placed in scintillation vials and soaked in 4 ml ethanol/methanol (3:1 v/v) for at least 45 minutes before addition of 10 ml liquid scintillator after which the samples are counted in a liquid scintillation counter.

Uptake inhibition is expressed as follows:

% inhibition =

$$\frac{\text{(Mean of group } E - \text{Value for test drug or imipramine)}}{\text{Mean of group } E - \text{Mean of group } F} \times 100$$

If the % inhibition given by the test compound at $10^{-5}$ M concentration is greater than or equal to that given by imipramine at $10^{-6}$ M concentration, the compound may be regarded as active. In this case a dose response experiment is carried out with the test compound and imipramine at concentrations of $10^{-5}$ M, $10^{-6}$ M and $10^{-7}$ M. The % inhibition is again calculated in the same way and the results are plotted as % inhibition against log compound concentration. The molar concentration which inhibits uptake by 50% (IC$_{50}$) is determined. The potency ratio compared to imipramine is calculated as:

$$\frac{IC_{50} \text{ of Imipramine}}{IC_{50} \text{ of Test Compound}}$$

The procedure for determining activity against noradrenaline uptake is similar save that $^3$H-noradrenaline at a concentration of $10^{-7}$ M is used instead of $^3$H-hydroxytryptamine. A test compound may be regarded as active if the % inhibition given at $10^{-6}$ M is at least that given by imipramine at $10^{-7}$ M.

The compounds of Examples 1 and 3 i.e. 5-hydroxy-N-[3-(theophyllin-7-yl)propyl]tryptamine hydrochloride hemihydrate and N-[3-theophyllin-7-yl)propyl]-tryptamine hydrochloride respectively, gave the following results in the above procedure.

| COMPOUND OF EXAMPLE NO. | INHIBITION OF 5-HYDROXY-TRYPTAMINE UPTAKE | | | POTENCY RATIO COMPARED WITH IMIPRAMINE | INHIBITION OF NORADRE-NALINE UPTAKE |
|---|---|---|---|---|---|
| | % INHIBITION AT | | | | |
| | 0.1 μM | 1 μM | 10 μM | | |
| 1 | 44% | 77% | 84% | 4.3 | INACTIVE |
| 3 | 4% | 43% | 77% | 0.8 | INACTIVE |

It will be seen that, in the 5-hydroxytryptamine tests, the compounds of Example 3 has about the same order of potency as the standard inhibitor imipramine whilst the compound of Example 1 is considerably more potent than imipramine. It will also be seen that the two compounds of the invention are active as inhibitors of 5-hydroxytryptamine (5-HT) uptake and inactive as inhibitors of noradrenaline (NA) uptake. The selectivity of the inhibition may be further examined by the following procedure.

PROCEDURE 2

Inhibition of 5-hydroxytryptamine and L-noradrenaline reuptake in rat cortical synaptosomes Ref: E. G. Gray and V. P. Whittaker (1962). J. Anat 96, p 79–88.

"The isolation of nerve endings from brain: An electron microscopic study of cell fragments dervied by homogenisation and centrifugation."

Test object: Purified rat cortical synaptosomes (P$_2$B) from 8–10 male albino rats (190–250 g).

Procedure: Rats are stunned and then killed by decapitation. The brain is quickly removed and the cortex excised essentially free of striatum and mid-brain. The tissue is then gently homogenised (10 strokes at 840 rpm) in 0.32 M sucrose. The homogenate of concentration 10% w/v in 0.32 sucrose is centrifuged at an average centrifugal force of 1000×g for 10 minutes and the supernatant is decanted and centrifuged at an average of 10000×g for 20 min to obtain the crude mitochondrial pellet (P$_2$). This fraction is resuspended by hand homogenisation in 0.32 M sucrose (3–4 ml) and layered on a sucrose density gradient comprising 0.8 M sucrose (10 ml):1.2 M sucrose (12 ml):3.0 M sucrose (5 ml). This is then centrifuged using a vertical rotor at an average of 201 000×g to 2.5×10$^{10}$ rad$^2$/S (approximately 35 mins). The purified synaptosomes (P$_2$B) are removed from the 0.8 M/1.2 M interface, and their volume made up to 50–60 ml with 0.32 M sucrose. The synaptosomes are then centrifuged in a swing-out rotor at 97 000×g average for 30 min. The resultant pellets are resuspended by hand homogenisation in 0.32 M sucrose. (2 ml/g original tissue). Throughout the procedure, it is essential to maintain the tissue and synaptosomes at 0.4° C. Synaptosomes should be used within three hours of preparation. A 100 μl aliquot of this synaptosomal suspension (2.5–3.0 mg protein/ml) is added to the incubation medium (900 μl) which has been preincubated at 37° C. for 5 min. The incubation medium which contains (final concentration): –($^3$H)-L-noradrenaline ($10^{-7}$ M), ($^{14}$C)-5-hydroxytryptamine ($10^{-7}$ M), NaCl (136 mM), KCl (5 mM), MgCl$_2$ (1.2 mM), CaCl$_2$ (2.5 mM), glucose (10 mM), ascorbate (1 mM), Tris (20 mM), is adjusted to pH 7.4 by the careful addition of HCl (aq) and gassed for 30 min with pure oxygen. All reagents are of 'Analar' grade and glass distilled water is used.

Test compounds may be present in 4 to 6 concentrations depending on previous experience, but normally the range would be $10^{-9}$ M to $10^{-6}$ M for an active compound. The quantity of material prepared per experiment would normally be sufficient to examine the effects of 30 different treatments (e.g. 6 compounds each at 5 concentrations in triplicate). The reaction continues at 37° C. for 4 min, and uptake is terminated by the addition of 2.4 ml incubation medium (less radiolabels) and rapid filtration under vacuum through 0.45 μm pore cellulose ester filters. The filters are then washed with 2.4 ml incubation medium. The radioactivity retained on the filter is determined by the addition of Instagel (10 ml) (Packard) and subsequent liquid scintillation counting to convert results into dpm. The non-specific binding and passive accumulation of both amines is corrected for by determining uptake in a sodium-free medium. Percentage inhibition of uptake is calculated as $$1 - \frac{\text{sample } dpm - \text{background } dpm}{\text{control } dpm - \text{background } dpm} \times 100\%$$

where background dpm is that accumulated in a sodium-free medium.

The data obtained is plotted as % inhibition against log compound concentration, and the concentration which inhibits uptake by 50% ($IC_{50}$) determined. Assays are run in triplicate, with 2 or 3 control and background determinations inserted randomly. The selectivity ratio is calculated as:

$$\frac{IC_{50} \, (NA \text{ uptake})}{IC_{50} \, (5\text{-}HT \text{ uptake})}$$

The following results were obtained in the procedure above:

| Compound | 5-HT Uptake $IC_{50}$ | NA Uptake $IC_{50}$ | Selectivity Ratio |
|---|---|---|---|
| Compound of Example 1 | $6 \times 10^{-8}$ M | $>10^{-5}$ M | >167 |
| imipramine | $1 \times 10^{-7}$ M | $5 \times 10^{-8}$ M | 0.5 |

It will be seen that the compound of Example 1 is not only a very potent inhibitor of 5-HT uptake, it is also very selective in its action.

The compounds having formula I and their pharmaceutically acceptable salts may be prepared by known reactions, in particular, by alkylation or reductive alkylation (where the alkyl group introduced may be substituted), reduction of a Schiff base, the Mannich reaction, removal of a protecting group or converting a compound having the formula I into a salt thereof or a salt into a compound having formula I.

The invention provides a process for the preparation of a compound having formula I or a pharmaceutically acceptable salt thereof, wherein (a) a compound having the formula

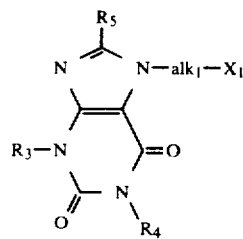

(II)

is reacted with a compound having the formula III

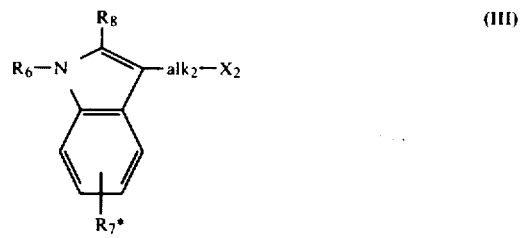

(III)

[wherein $R_3$, $R_4$, $R_5$, $R_6$ and $R_8$ are as defined with respect to formula I; one of $X_1$ and $X_2$ is a leaving group or atom; the other one of $X_1$ and $X_2$ is a group having the formula IV

(wherein $R_1$, $R_2$ and a are as defined with respect to formula I) or a salt thereof at the nitrogen atom marked with an asterisk; $R_7^*$ is the same as $R_7$ as defined with respect to formula I save that hydroxy may, if desired, be in salt form or protected with a removable protecting group; and $alk_1$ and $alk_2$ are as defined with respect to formula I such that a hydrogen atom is carried by the carbon atom linked directly to the said leaving group or atom] and, where necessary, a removable protecting group is removed;

or (b) a compound having the formula V

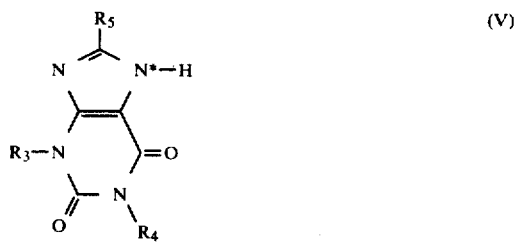

(V)

[wherein $R_3$, $R_4$ and $R_5$ are as defined above] or a salt thereof at the nitrogen atom marked with an asterisk is reacted with a compound having the formula VI

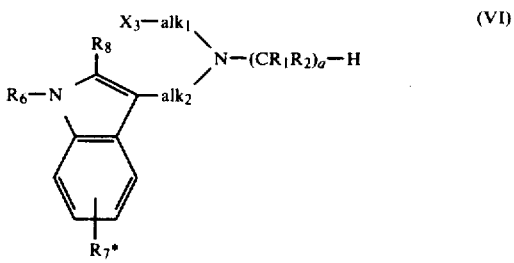

(VI)

[wherein $X_3$ is a leaving atom or group; $alk_2$, $R_1$, $R_2$, a, $R_6$ and $R_8$ are as defined above with reference to formula I, $R_7^*$ is as defined above with respect to formula III and $alk_1$ is as defined above with respect to formula I subject to the proviso that a hydrogen atom is carried by the carbon atom linked directly to $X_3$] and, where necessary, a removable protecting group is removed; or (c) a compound having the formula VII

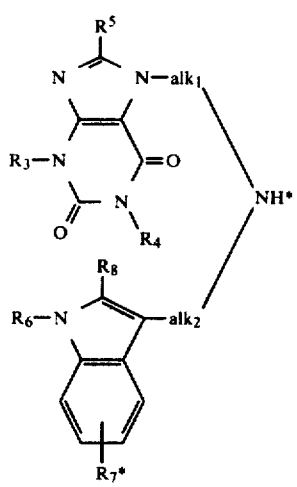

[wherein alk₁, alk₂, R₃, R₄, R₅, R₆, R₇* and R₈ are as defined above] or a salt thereof at the nitrogen marked with an asterisk is reacted with a compound having the formula VIII $$X_3-CR_1R_2-H \qquad (VIII)$$

[wherein X₃, R₁, and R₂ are as defined above] and, where necessary, a removable protecting group is removed; or (d) a compound having the formula IX $$Y_1-NH-(CR_1R_2)_a-H \qquad (IX)$$

is reductively condensed with a carbonyl compound having the formula X

[wherein R₁, R₂ and a are as defined above and Y₁, Y₂ and Y₃ are such that one of Y₁ and —CHY₂Y₃ denotes a group having the formula XI

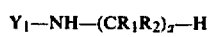

and the other one of Y₁ and —CHY₂Y₃ is a group having the formula XII

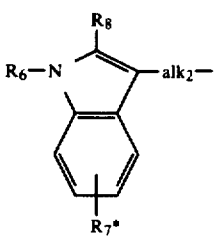

(wherein R₃, R₄, R₅, R₆, R₇*, R₈, alk₁ and alk₂ are as defined above)] and, if necessary, a removable protecting group is removed; or (e) a Schiff base having the formula XIII

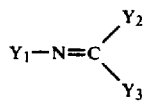

[wherein Y₁, Y₂ and Y₃ are as defined above] is reduced and, where necessary, a removable protecting group is removed; or (f) a compound having the formula V

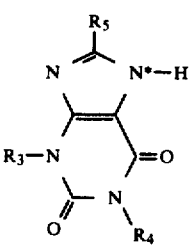

[wherein R₃, R₄ and R₅ are as defined above] is reductively condensed with a carbonyl compound having the formula XIV

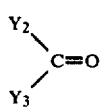

[wherein Y₄ and Y₅ are such that the group having the formula —CHY₄Y₅ is the same as the group having the formula VI as defined and illustrated above save that X₃ is a direct bond] and, where necessary, a removable protecting group is removed; or (g) a compound having the formula VII as hereinbefore defined and illustrated is reductively condensed with a carbonyl compound having the formula XV $$R_1R_2C=O \qquad (XV)$$

[wherein R₁ and R₂ are as defined above] and, if necessary, a removable protecting group is removed; or (h) a compound having the formula V

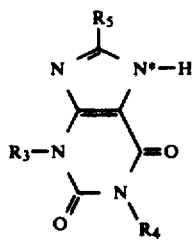 (V)

[wherein $R_3, R_4$ and $R_5$ are as defined above] or a salt thereof at the nitrogen atom marked with an asterisk is reacted with an aziridine or aziridinium salt having the formula XV or XVII

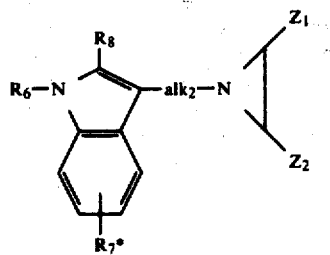 (XV)

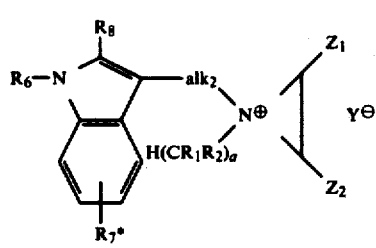 (XVII)

[wherein $R_1$, $R_2$, $R_6$, $R_7^*$, $R_8$, a and $alk_1$ are as defined above; $Z_1$ and $Z_2$ are, independently, hydrogen or lower alkyl such that the total number of carbon atoms in $Z_1$ and $Z_2$ is from 0 to 4 and Y is an anion] and, if necessary, a removable protecting group is removed; or (i) a compound having the formula XVIII

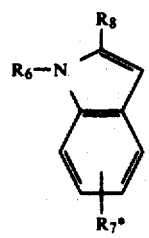

[wherein $R_6$, $R_7^*$ and $R_8$ are as defined above] is reacted with (1) an aldehyde having the formula IXX $R_9CHO$ (IXX)

[wherein $R_9$ is hydrogen or methyl] and an amine having the formula XX

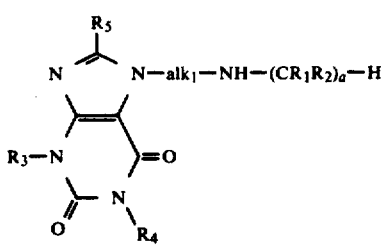 (XX)

[wherein $R_1, R_2, R_3, R_4, R_5$, $alk_1$ and a are as defined above] or a salt thereof; or (2) an imine or iminium salt having the formula XXI or XXIA

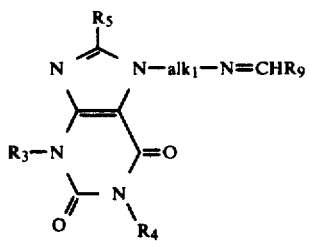 (XXI)

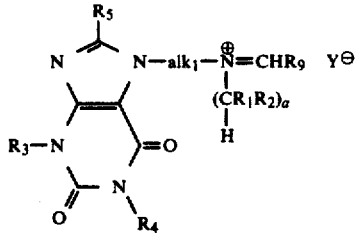 (XXXIA)

[wherein Y, $R_1, R_2, R_3, R_4, R_5, R_9$, $alk_1$ and a are as defined above] and, where necessary, a removable protecting group is removed; or (j) a compound having the formula XXII or XXIII

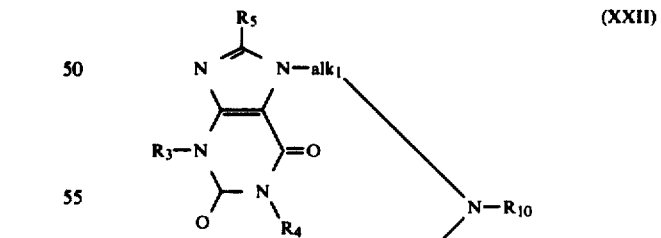 (XXII)

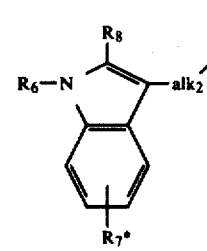

-continued

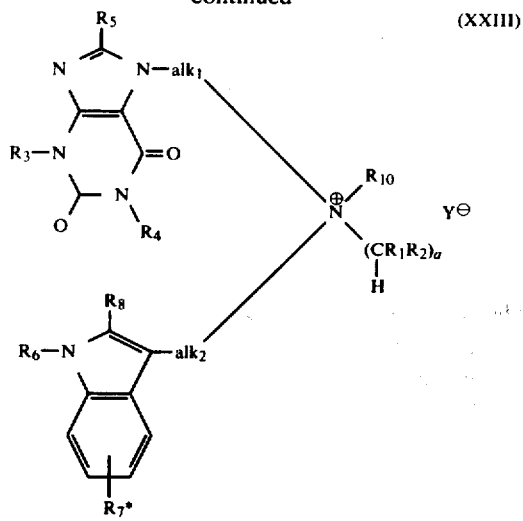

(XXIII)

[wherein $R_1, R_2, R_3, R_4, R_5, R_6, R_7^*, R_8$, $alk_1$, $alk_2$, Y and a are as defined above and $R_{10}$ is a removable protecting group] is subjected to treatment to remove $R_{10}$ and, where necessary, a protecting group in $R_7^*$ is also removed; or (k) a compound having the formula XXIV

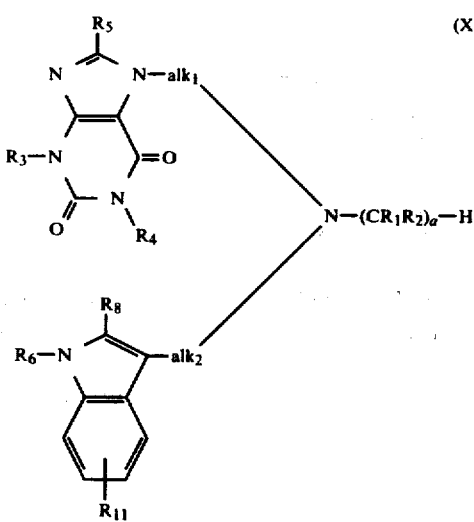

(XXIV)

or an acid addition salt thereof [wherein $R_1$, $R_2$, $R_3$, $R_4$, $R_5$, $R_6$, $R_8$, $alk_1$, $alk_2$ and a are as defined above and $R_{11}$ is hydroxy protected by a removable protecting group] is subjected to treatment to remove the removable protecting group.

Where desired, the process may also include the conversion of a compound having formula I into a pharmaceutically acceptable salt thereof or conversion of a salt of a compound having formula I into a compound having formula I.

By the term "removable" as applied to protecting groups herein there is meant that the group may be removed without destroying the compound having formula I or a salt thereof. In particular it may be noted that formula I includes amide functions in the xanthine ring system. It is therefore recommended to avoid any prolonged exposure to strongly alkaline or strongly acid conditions whereby such an amide function may hydrolyse.

The compounds of the general formula I may contain one or more asymmetric carbon atoms, for instance, in the case when $alk_1$ or $alk_2$ is propylene. Thus compounds of the invention may exist as optically active forms or mixtures thereof, especially racemic mixtures. Mixtures of stereoisomers may be separated in known manner, for instance, by fractional crystallisation. In particular optically active compounds may be obtained by recrystallisation of a salt of racemic free bases of formula I with optically active acids. Individual stereoisomers may also be obtained by using optically active starting materials in the process of the invention.

Step (a) of the process of the invention can be carried out in known manner for converting primary amines into secondary amines into tertiary amines. As the leaving group or atom there may be used an organosulphonyloxy group (for instance methane sulphonyloxy or p-toluenesulphonyloxy) or halogen (for instance, chlorine or bromine). Where $alk_2$ is methylene linked to a leaving group or atom as $X_2$, then $X_2$ may be a disubstituted amino group such as dimethylamino or a trisubstituted ammonium group such as $—N^{\oplus}(CH_3)_3$. The compounds having the formulae II and III are generally known and, where new, may be prepared in known manner.

The reaction of step (a) may be carried out without addition of a solvent or, preferably, in the presence of a solvent or dispersion medium. As solvents or dispersion media there may be mentioned aromatic hydrocarbons such as benzene, toluene, xylene; ketones such as acetone or methylethylketone; halogenated hydrocarbons such as chloroform, carbon tetrachloride or methylene chloride; ethers such as tetrahydrofuran and dioxane; sulphoxides such as dimethylsulphoxide; tertiary acid amides such as dimethylformamide and N-methylpyrrolidone; alcohols such as methanol, ethanol, isopropanol, amyl alcohol etc. The reaction may be carried out at a temperature within the range of 20°–200° C., preferably 50°–180° C. Normally the reaction will be carried out using a free amine as one of the reactants. In this case it is usually recommended to carry out the reaction in the presence of a weak base, for instance, an alkali metal carbonate or a tertiary amine. Alternatively, the reaction may be carried out using a salt of the amine, for instance, the lithium salt.

Such a lithium salt may be prepared by reaction of the amine with an organolithium compound, for instance, butyl lithium. Where such a salt is to be prepared the starting amine should, of course, be such that the salt is formed at the nitrogen atom marked with an asterisk. Salt formation at the wrong site is prevented by ensuring that the amine contains no other nitrogen atom carrying a hydrogen atom. For instance, where the amine is of formula II, $R_3$ and $R_4$ should be lower alkyl or, where the amine is of formula III, $R_6$ should be lower alkyl.

Where the compound having formula III is such that $R_7^*$ is hydrogen, it has been found that yields may be low. The yield may be enhanced by using a compound in which the hydroxy is protected with a removable protecting group. For instance, $R_7^*$ may be benzyloxy or acetoxy. The benzyl group may be removed by catalytic hydrogentation. The acetyl group may be removed by alkaline hydrolysis under mild conditions, for instance with aqueous ammonia.

Process step (b) may be carried out under similar reaction conditions to step (a). $X_3$ may be halogen (for instance chlorine or bromine) or organosulphonyloxy. Compounds having the formula V are generally known, e.g. Chem. Abs. 48, 1347d (1954) and 47, 4920g (1953), and commercially available in some cases (xanthine and theophylline). Compounds having the general formula VI are generally new and may be prepared in known manner, for instance, according to the following reaction scheme where $X_3$ is bromine

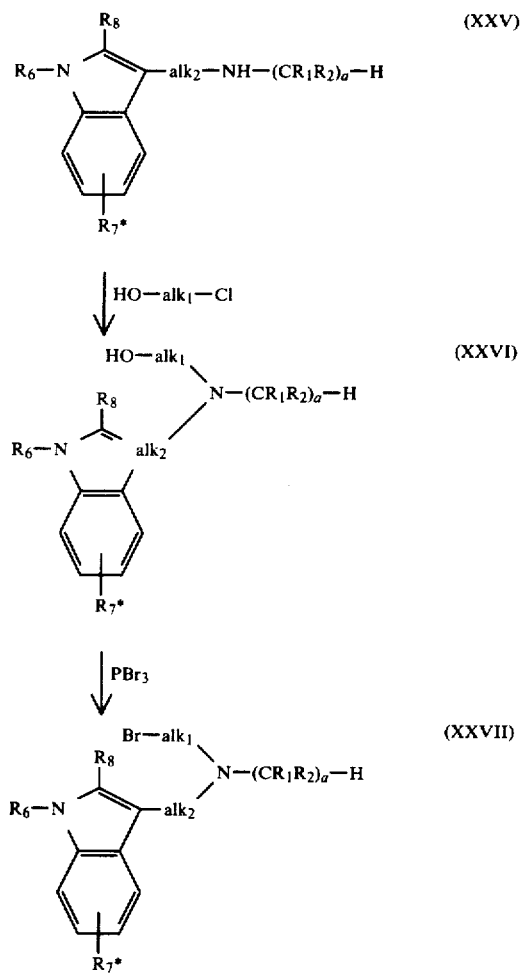

Where $alk_1$ is ethylene or substituted ethylene whilst a is 0, the bromine compound XXVII may react with itself to form an aziridine of formula XV. In this case the aziridine may be used for reaction with the compound having formula V [see process step (h)].

Process step (c) can be carried out under similar reaction conditions to step (a). $X_3$ may be halogen, preferably chlorine or bromine, or organosulphonyloxy. Compounds having the formula VIII are generally known. Compounds having the formula VII are generally new. They may be prepared in known manner, for instance, according to step (a) or (b) wherein the symbol a is 0.

Process steps (d), (f) and (g) are preferably carried out by catalytic hydrogenation. The reductive condensation may be carried out at room temperature under normal pressure or high pressure. The reaction may be carried out in such solvents as alcohols, water/alcohol mixtures, dimethylformamide etc. As catalysts there may be used platinum, palladium or nickel with or without a carrier. For a reference on the reductive condensation of amines with carbonyl compounds, see Organic Reactions, Vol. 4, pp. 174-255 (1948) published by John Wiley & Sons, Inc.

Where $R_7^*$ in the starting material represents hydroxy protected by a protecting group removable by catalytic hydrogenation, e.g. benzyloxy, this protecting group may also be removed under the conditions used for the reductive condensation thereby eliminating a separate after-step for the removal. Where $R_7^*$ in the starting material is hydroxy protected by a protecting group removable under mild hydrolytic conditions, eg. acetyloxy, then an after-step is needed to secure the compound of the invention.

The reductive condensation may be carried out by performing the reduction during or after condensation. When, in the case of process (d) where symbol a is 0, the condensation is carried out before reduction, it may be possible to isolate the condensation product intermediate as a Schiff base which in turn may be reduced. Thus step (g) of the process of the invention involves reduction of a Schiff base. The reduction may be carried out by catalytic hydrogenation or with sodium borohydride as reducing agent. The procedure may be illustrated by the use of indole-3-aldehyde according to the following reaction scheme:

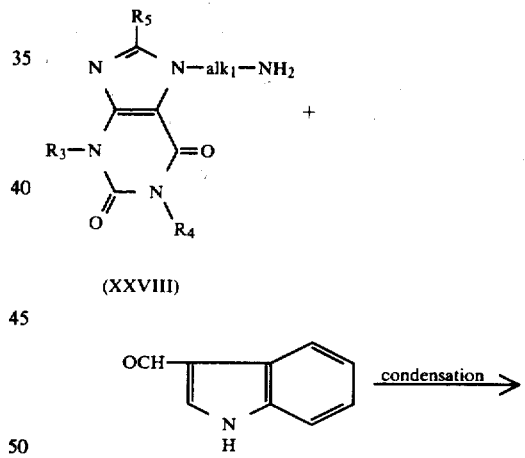

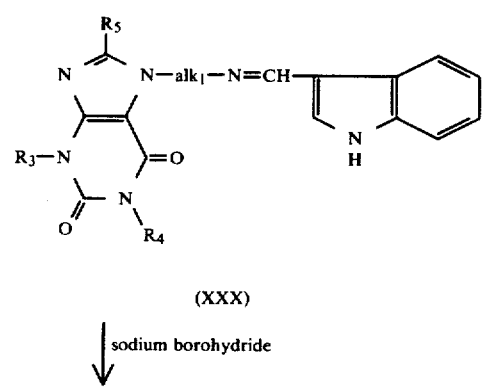

-continued

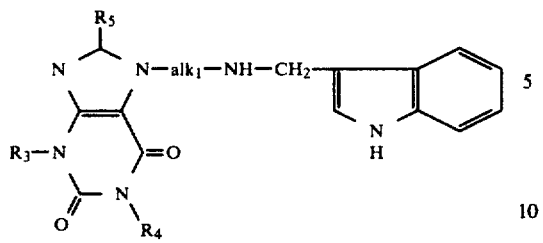

(XXXI)

A solution of indole-3-aldehyde (XXIX) and an equivalent amount of the amine (XXVIII) in toluene or xylene is refluxed under a water-separator for as long as is needed to collect about the theoretical quantity of water. The hot solution is then filtered and evaporated to dryness to yield the Schiff base (XXX) in crude form. The Schiff base need not be purified. It is dissolved in ethanol and sodium borohydride is added to the solution to effect the reduction to yield product (XXXI).

The carbonyl compounds having formulae X,XIV and XV are sometimes known e.g. in the case of formulae XV and XXIX, and sometimes new. Novel carbonyl compounds may be prepared in known manner.

Process (h) comprises the reaction of a compound having formula V or a salt thereof with an aziridine or aziridinium salt of formula XV or XVI. The compounds having formula XV and XVI are generally new and may be prepared in known manner for the preparation of aziridines and aziridinium salts. The reaction may be carried out in a solvent such as dimethylformamide at room temperature or elevated temperature.

Step (i) comprises the Mannich reaction. The starting materials for the reaction are known or, if new, can be prepared in known manner. The reaction may be carried out using such solvents as water, dioxane, alcohols such as isopropanol and acetic acid at temperatures which may be between 0° and 70° C. Where the indole is reacted with an aldehyde and an amine, the aldehyde is preferably formaldehyde. Formaldehyde may be employed as either paraformaldehyde or as a solution. The amine is preferably a secondary amine, i.e. a=1, but a primary amine may be used. The reaction may use the amine in free form or salt form but we prefer to use acid conditions so that the amine will be in salt form. Non-acidic conditions are not normally desirable since the basic side chain substituent on the indole nucleus may be introduced at the wrong site, e.g. the 1-position, in the absence of an acid where $R_6$ is hydrogen. Whilst it is possible to react the indole (XVIII) directly with the aldehyde (XIX) and the amine (XX), the reaction may also be carried by preforming an imine (XXI) or an iminium compound (XXXIA). For instance an iminium compound (XXIA) may be formed reacting the amine and aldehyde together in the presence of an acid (HY), preferably acetic acid, and then the iminium compound is reacted with the indole according to the following reaction scheme:

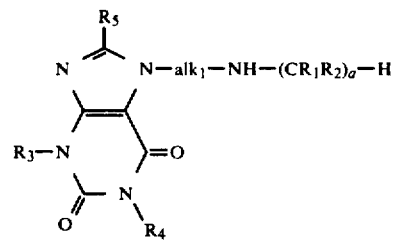

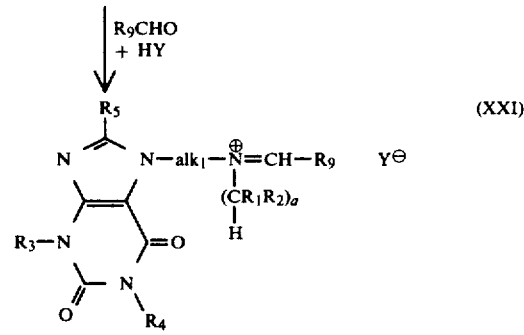

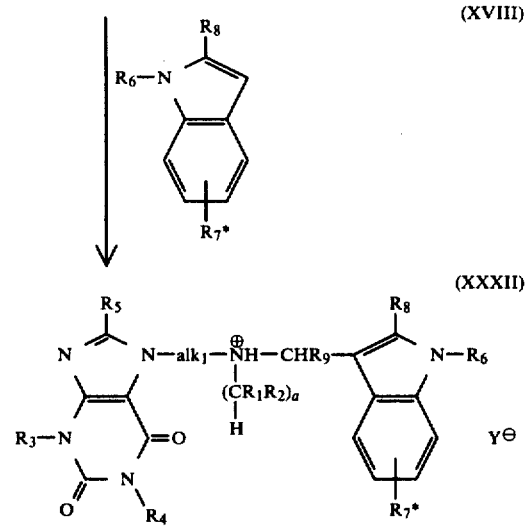

Process steps (j) and (k) involve the removal of a protecting group from a nitrogen atom and/or an oxygen atom. As the protecting group for nitrogen we prefer to use a group removable by hydrogenation, for instance, mono- or di-arylmethyl, preferably benzyl. A benzyl group may also be used as protecting group on the oxygen atom. Again hydrogenation is used to remove the benzyl group. Alternatively hydroxy may be protected as a lower alkanoyloxy group, for instance, acetoxy. The alkanoyl group may be removed by means aqueous or alcoholic ammonia. The compounds having formulae XXII, XXIII and XXIV are new compounds. They may be prepared using one of steps (a) to (d) or by methods known per se. The preparation of such compounds and the use of steps (j) and (k) may be illustrated by the following synthesis for the preparation of 5-hydroxy-N-[3-theophyllin-7-yl)propyl]tryptamine.

N-Benzyl-5-benzyloxytryptamine, which can be prepared by the procedure of Speeter and Anthony, J.A.C.S., 76, 6208 (1954) by reacting 5-benzyloxy-3-indol-glyoxylyl chloride with benzylamine and reducing the product with lithium aluminium hydride, is reacted with 3-(theophyllin-7-yl)propyl bromide in the presence of a weak base such as potassium carbonate to yield N-benzyl-5-benzyloxy-N-[3-theophyllin-7-yl)propyl]tryptamine. Debenzylation by hydrogenation in the presence of a platinum catalyst gives the desired compound. By starting from 5-acetoxy-3-indolglyoxylyl chloride instead of 5-benzylox-3-indol-glyoxylyl chloride and proceeding in analogous manner 5-acetoxy-N-[3-(theophyllin-7-yl)propyl]tryptamine is prepared. Treatment of this compound with ammonia solution to remove the acetyl group gives the desired compound.

Where a compound having the formula I has been prepared, it may be converted into a pharmaceutically acceptable salt thereof in standard manner. For instance addition of ethanolic hydrogen chloride gives the hydrochloride acid addition salt. A salt of a compound having the formula I may be converted into a compound having formula I in standard-manner. For instance treatment of an acid addition salt with a cooled aqueous solution of a base yields the amine in free form.

This invention also includes pharmaceutical compositions containing as active ingredient an active compound of formula I as above defined or a pharmaceutically acceptable salt thereof. The active compound may be finely comminuted if desired. In addition to the active ingredient, the compositions also contain a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an excapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient.

Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of composition, for example packeted powders or vials or ampoules. The unit dosage form can be a capsule, cachet, or tablet itself, or it can be the appropriate number of any of these in package form. The quantity of active ingredient in a unit dose of composition may be varied or adjusted from 5 mg or less to 500 or more, according to the particular need and the activity of the active ingredient. The invention also includes the compounds in the absence of carrier where the compounds are in unit dosage form.

The following Examples illustrate the invention:

EXAMPLE 1

5-Hydroxy-N-[3-(theophyllin-7-yl)propyl]tyrptamine

A suspension of 3-(theophyllin-7-yl)propyl bromide (3.01 g. 0.01 mole) and potassium carbonate (5.2 g. 0.037 mole) in dimethylformamide (30 cc.) was heated to 75° C. and degassed with nitrogen. 5-Hydroxytryptamine acid oxalate salt (2.66 g., 0.01 mole) was added and the mixture was stirred well at 75° C. for 23¼ hours under a blanket of nitrogen. The reaction mixture was cooled and diluted with water (250 cc.). Chloroform (50 cc.) was added. The black mixture was well stirred for about 2½ hours and filtered to remove some black tar. The tar was washed well with chloroform (50 cc.) and the organic layer was separated. The aqueous phase was washed with chloroform (2×50 cc.). The aqueous phase was discarded and the organic layers were combined and dried with magnesium sulphate. The mixture was filtered and evaporated to give a brown oil (2.6 g.). This oil was dissolved in ethanol (6 cc.), acidified with ethanolic hydrogen chloride and cooled to give a gummy black tar and crystals. The crystals were redissolved upon heating and the mixture was diluted to about 25 cc. with boiling ethanol, decanted from the tar, washed with more ethanol and cooled. The mixture was filtered and the grey precipitate washed well with ethanol. The solid was triturated with boiling ethanol/methanol, cooled in ice, filtered and the filtered precipitated was washed with ice-cold ethanol and dried in an oven at 80° C./1 mm. pressure overnight to yield a solid of melting point 253°–257° C. The solid was recrystallised (with filtering hot) from water/methanol, cooled in ice, diluted with ethanol and kept at 0° C. for 3 hours under nitrogen, filtered and the filtered precipitate was washed with cold ethanol. This precipitate was combined with a second crop obtained on leaving the filtrate to stand overnight at room temperature to provide 0.44 g. of 5-hydroxy-N-[3-(theophyllin-7-yl)propyl] tryptamine hydrochloride hemihydrate, m.p. 260°–265° C. (dec.) (softens above 255° C.). The product may also be designated as 3,7-dihydro-7-[3-([2-(5-hydroxy-1H-indol-3-yl)ethyl]amino)propyl]-1,3-dimethyl-1H-purine-2,6-dione, hydrochloride, hemihydrate.

Analysis Calculated for $C_{20}H_{24}N_6O_3 \cdot HCl \cdot \frac{1}{2}H_2O$: C, 54.35%; H, 5.93%; N, 19.02%. Found: C, 54.50%; H, 6.05%; N, 19.05%.

EXAMPLE 2

5-Benzyloxy-N-[3-theophyllin-7-yl)propyl]tryptamine

A mixture of 3-(theophyllin-7-yl)propyl bromide (1 g., 3.2 millimole), potassium carbonate (3 g., 21.7 millimole) and 5-benzyloxytryptamine hydrochloride (1.0 g., 3.3 millimole) in dry dimethylformamide (20 cc.) was stirred under dry nitrogen in an oil bath maintained at 75° C. for 17½ hours. The mixture was cooled under nitrogen, diluted with water (100 cc.) and extracted with chloroform (2×50 cc.). The combined extracts were washed with water (2×50 cc.) and dried ($MgSO_4$) to give a pale yellow solution. The solution was filtered and evaporated to give a gum, which was dissolved in a little ethanol and acidified with ethanolic hydrogen chloride. A solid set at once. The mixture was allowed to cool and filtered. The precipitate was washed with ethanol and then with ethyl acetate to give very pale yellow crystals, m.p. 135°–145° C. (dec.), which were dried in an oven at 80° C./100 mm. pressure. The yield of title compound as the dihydrochloride quarterhydrate was 1.15 g. The product may also be designated as 7-[3-([2-(5-benzyloxy-1H-indol-3-yl)ethyl]amino)-propyl]-3,7-dihydro-1,3-dimethyl-1H-purine-2,6-dione, dihydrochloride quarterhydrate.

Analysis: Calculated for $C_{27}H_{30}N_6O_3 \cdot 2HCl \cdot \frac{1}{4}H_2O$: C, 57.50%; H, 5.81%; N, 14.90%. Found: C, 57.34%; H, 5.94%; N, 15.19%.

EXAMPLE 3

N-[3-(Theophyllin-7-yl)propyl]tryptamine

A stirred mixture of 3-(theophyllin-7-yl)propyl bromide (3.0 g., 0.01 mole), tryptamine base (1.60; 0.01 mole) and potassium carbonate (4 g; 0.029 mole) in dry dimethylformamide (50 cc.) was heated, under a dry nitrogen blanket, in an oil-bath maintained at 75° for 17.5 hours. After cooling, the dark mixture was diluted with water (200 cc.) and extracted with dichloromethane (2×50 cc.). The combined extracts were washed with water (2×100 cc.) and dried ($MgSO_4$). Filtration and evaporation gave a syrup which was dissolved in a little ethanol and acidified with ethanolic hydrogen chloride. After cooling, the precipitated crystals were filtered off and washed well with ethanol and ethyl acetate to give the title compound hydrochloride, m.p. 273°–274° C. (dec.) (partial decomposition above 265° C.). The product may also be designated as 3,7-dihydro-7-[3-[[2-(1H-indol-3-yl)ethyl]amino]propyl]-1,3-dimethyl-1H-purine-2,6-dione,hydrochloride. The yield was 1.99 g.

Analysis: Calculated for $C_{20}H_{24}N_6O_2 \cdot HCl$ C, 57.61%; H, 6.04%; N, 20.16% Found: C, 57.46%; H, 6.33%; N, 20.13%.

EXAMPLE 4

Reaction of the following halogen compounds with the following amines in the presence of potassium carbonate in dimethylformamide yields the stated products:

| Halogen Compound | Amine | Product |
|---|---|---|
| Methyl iodide | Title compound of Example 1 | 5-Hydroxy-N—methyl-N—[3-(theophyllin-7-yl)propyl]tryptamine |
| 3-(Xanthin-7-yl)propyl bromide | 5-Ethoxy-tryptamine | 5-Ethoxy-N—[3-(xanthin-7-yl)propyl]tryptamine |
| 2-(Theophyllin-7-yl)ethyl bromide | 5-Methoxy-tryptamine | 5-Methoxy-N—[2-(theophyllin-7-)ethyl]tryptamine |
| 4-(Theophyllin-7-yl)butyl bromide | 6-(Dimethyl-amino)homo-tryptamine | 6-(Dimethylamino)-N—[4-(theophyllin-7-yl)butyl]homotryptamine |
| 3-(Theophyllin-7-yl)propyl bromide | 1,6-dimethyl-tryptamine | 1,6-Dimethyl-N—[3-(theophyllin-7-yl)propyl]tryptamine |
| 3-(Theophyllin-7-yl)propyl bromide | 5-Chloro-2-methyltrypta-mine | 5-Chloro-2-methyl-N—[3-(theophyllin-7-yl)propyl]tryptamine |
| 3-(Theophyllin-7-yl)propyl bromide | 5-(Trifluoro-methyl)trypta-mine | N—[3-(Theophyllin-7-yl)propyl]-5-(tri-fluoromethyl)trypta-mine |

We claim:
1. A compound selected from those having the formula I

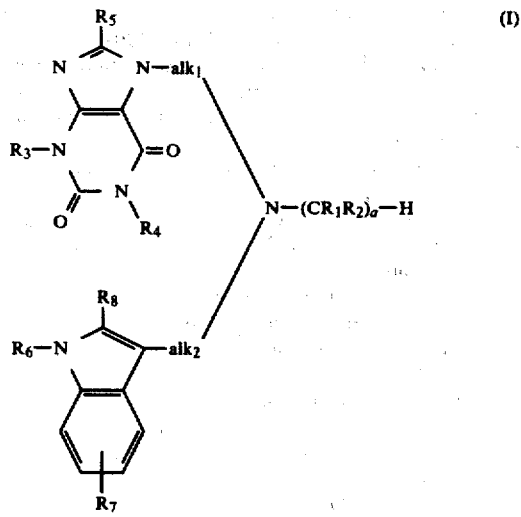

and their pharmaceutically acceptable salts, wherein
  $alk_1$ and $alk_2$ are, independently, lower alkylene which may be a straight or branched chain, either one or both of $alk_1$ and $alk_2$ includes a hydrogen atom carried by the carbon atom linked directly to the nitrogen atom bearing —$(CR_1R_2)_aH$;
  $R_1$ and $R_2$ are independently so selected from hydrogen and alkyl that —$CHR_1R_2$ is lower alkyl;
  a is selected from 0 and 1;
  $R_3$, $R_4$, $R_5$, $R_6$ and $R_8$ are independently selected from hydrogen and lower alkyl; and
  $R_7$ is selected from hydrogen, hydroxy, lower alkoxy, phenyl(lower)alkoxy, lower alkyl, halogen, trifluoromethyl and di(loweralkyl)amino.

2. A compound as claimed in claim 1, wherein $R_1$, $R_2$, $R_3$, $R_4$, $R_5$ and $R_8$ are each independently selected from hydrogen and methyl.

3. A compound as claimed in claim 1, wherein $alk_1$ and $alk_2$ are independently selected from ethylene and trimethylene.

4. A compound as claimed in claim 1 wherein $R_7$ is hydroxy, lower alkoxy or phenyl(lower)alkoxy in the 5-position.

5. A compound as claimed in claim 1 which is selected from 5-hydroxy-N-[3-theophyllin-7-yl)propyl]-tryptamine and the pharmaceutically acceptable salts thereof.

6. A compound as claimed in claim 1, which is selected from 5-benzyloxy-N-[3-theophyllin-7-yl)propyl]-tryptamine and the pharmaceutically acceptable salts thereof.

7. A compound as claimed in claim 1, which is selected from N-[3-(theophyllin-7-yl)propyl]tryptamine and the pharmaceutically acceptable salts thereof.

8. A pharmaceutical composition comprising an antidepressively active amount of a compound as claimed in claim 1 in association with a pharmaceutically acceptable carrier.

* * * * *